(12) United States Patent
Kurimoto

(10) Patent No.: US 12,635,900 B2
(45) Date of Patent: May 26, 2026

(54) ELECTRIC EQUIPMENT

(71) Applicant: PACIFIC INDUSTRIAL CO., LTD., Ogaki (JP)

(72) Inventor: Masaru Kurimoto, Ogaki (JP)

(73) Assignee: PACIFIC INDUSTRIAL CO., LTD., Ogaki (JP)

( * ) Notice: Subject to any disclaimer, the term of this patent is extended or adjusted under 35 U.S.C. 154(b) by 303 days.

(21) Appl. No.: 18/689,658

(22) PCT Filed: Oct. 28, 2022

(86) PCT No.: PCT/JP2022/040343
§ 371 (c)(1),
(2) Date: Mar. 6, 2024

(87) PCT Pub. No.: WO2023/176036
PCT Pub. Date: Sep. 21, 2023

(65) Prior Publication Data
US 2024/0358274 A1 Oct. 31, 2024

(30) Foreign Application Priority Data

Mar. 17, 2022 (JP) ................................. 2022-042173

(51) Int. Cl.
*A61B 5/07* (2006.01)
*A01K 11/00* (2006.01)
*A01K 29/00* (2006.01)
(52) U.S. Cl.
CPC .............. *A61B 5/07* (2013.01); *A01K 11/007* (2013.01); *A01K 29/005* (2013.01); *A61B 2503/40* (2013.01); *A61B 2560/0209* (2013.01)
(58) Field of Classification Search
None
See application file for complete search history.

(56) References Cited

U.S. PATENT DOCUMENTS 7,617,001 B2 * 11/2009 Penner ............... A61N 1/37217
607/30
9,900,669 B2 * 2/2018 Touma ..................... H04Q 9/00
(Continued)

FOREIGN PATENT DOCUMENTS

CN 206226464 U 6/2017
CN 110799099 A 2/2020
(Continued)

OTHER PUBLICATIONS

Aug. 27, 2025 Office Action issued in Chinese Patent Application No. 202280060157.6.
(Continued)

*Primary Examiner* — Muhammad Adnan
(74) *Attorney, Agent, or Firm* — Oliff PLC

(57) ABSTRACT

Electric equipment includes: a command input unit to which a switching command is input contactlessly from an outside; and a mode switcher to switch an electric circuit between a normal operation mode and a sleep mode in response to the switching command. The normal operation mode includes the normal operation mode in an unlocked state and the normal operation mode in a locked state in which switching to the sleep mode is prohibited. The switching command includes: a first switching command for switching to the sleep mode, a second switching command for switching to the normal operation mode in the unlocked state, and a third switching command for switching to the normal operation mode in the locked state, having a longer input time than the second switching command. The switching command uses magnetism, light, or a sound wave as a carrier. The command input unit includes a carrier detection sensor.

19 Claims, 6 Drawing Sheets

(56)    References Cited

U.S. PATENT DOCUMENTS

|  |  |  |  |  |
|---|---|---|---|---|
| 12,402,606 | B2 * | 9/2025 | Loh | A61B 5/07 |
| 2006/0142819 | A1 * | 6/2006 | Penner | A61B 5/1112 |
|  |  |  |  | 607/32 |
| 2007/0088194 | A1 * | 4/2007 | Tahar | A61B 5/0031 |
|  |  |  |  | 600/102 |
| 2007/0161873 | A1 * | 7/2007 | Ni | G16H 50/20 |
|  |  |  |  | 600/300 |
| 2015/0290465 | A1 * | 10/2015 | Mashiach | A61N 1/3787 |
|  |  |  |  | 607/61 |
| 2016/0038086 | A1 | 2/2016 | Wrigglesworth et al. | |
| 2017/0042119 | A1 * | 2/2017 | Garrity | G01S 5/0294 |
| 2017/0095206 | A1 * | 4/2017 | Leib | A61B 5/14542 |
| 2017/0272842 | A1 | 9/2017 | Touma et al. | |
| 2018/0310522 | A1 * | 11/2018 | Bancroft | H04B 1/0458 |
| 2021/0327107 | A1 | 10/2021 | Behrooz | |
| 2022/0000388 | A1 | 1/2022 | Astl et al. | |
| 2024/0273785 | A1 | 8/2024 | Behrooz | |
| 2024/0407332 | A1 * | 12/2024 | Biffert | A01K 29/005 |

FOREIGN PATENT DOCUMENTS

|  |  |  |  |
|---|---|---|---|
| CN | 111970960 | A | 11/2020 |
| CN | 212489866 | U | 2/2021 |
| CN | 113556936 | A | 10/2021 |
| JP | 2007-108855 | A | 4/2007 |
| JP | 2010-160194 | A | 7/2010 |
| JP | 2011-086411 | A | 4/2011 |
| JP | 2011-123792 | A | 6/2011 |
| JP | 2016-144428 | A | 8/2016 |
| JP | 2018-093887 | A | 6/2018 |
| JP | 2019-150587 | A | 9/2019 |
| JP | 2021-174372 | A | 11/2021 |

OTHER PUBLICATIONS

Dec. 20, 2022 Search Report issued in International Patent Application No. PCT/JP2022/040343.
May 24, 2022 Office Action issued in Japanese Patent Application No. 2022-042173.

* cited by examiner

ELECTRIC EQUIPMENT

TECHNICAL FIELD

The present disclosure relates to electric equipment capable of switching an operation state of an electric circuit between a sleep mode and a normal operation mode.

BACKGROUND ART

As this type of conventional electric equipment, there has been known electric equipment that switches an operation state contactlessly from the outside (see, for example, Patent Document 1).

RELATED ART DOCUMENTS

Patent Documents

Patent Document 1: JP 2011-086411 A (paragraphs [0008], [0014], FIG. 2, and the like)

SUMMARY OF THE INVENTION

Problems to be Solved by the Invention

However, in a case where the operation state is switched contactlessly, there is a problem that the operation state is switched unintentionally under the influence of disturbance. A need exists for countermeasures against the problem.

Means of Solving the Problems

Electric equipment according to a first aspect of the present disclosure made to solve the above problem includes: a command input unit to which a switching command is input contactlessly from an outside; and a mode switcher configured to switch an electric circuit of the electric equipment between a normal operation mode and a sleep mode in response to the input switching command, wherein the normal operation mode includes the normal operation mode in an unlocked state in which switching to the sleep mode is allowed, and the normal operation mode in a locked state in which switching to the sleep mode is prohibited, and the switching command includes a first switching command for switching the normal operation mode to the sleep mode, a second switching command for switching the sleep mode to the normal operation mode and keeping the normal operation mode in the unlocked state, and a third switching command for switching the sleep mode to the normal operation mode and keeping the normal operation mode in the locked state. The third switching command has a longer input time or a more complicated input mode to the command input unit than an input time or an input mode of the second switching command. The switching command uses any one of magnetism, light, or a sound wave as a carrier. The command input unit includes a carrier detection sensor configured to detect the carrier, and the switching command has a different command content depending on a difference in a detection length that is a time during which the carrier detection sensor continuously detects the carrier. The switching command having the detection length shorter than a predetermined reference length is the second switching command, and the switching command having the detection length equal to or longer than the reference length is the third switching command.

Electric equipment according to a second aspect of the present disclosure includes: a command input unit to which a switching command is input contactlessly from an outside; and a mode switcher configured to switch an electric circuit of the electric equipment between a normal operation mode and a sleep mode in response to the input switching command, wherein the normal operation mode includes the normal operation mode in an unlocked state in which switching to the sleep mode is allowed, and the normal operation mode in a locked state in which switching to the sleep mode is prohibited, and the switching command includes a first switching command for switching the normal operation mode to the sleep mode, a second switching command for switching the sleep mode to the normal operation mode and keeping the normal operation mode in the unlocked state, and a third switching command for switching the sleep mode to the normal operation mode and keeping the normal operation mode in the locked state. The third switching command has a longer input time or a more complicated input mode to the command input unit than an input time or an input mode of the second switching command. The switching command uses any one of magnetism, light, or a sound wave as a carrier. The command input unit includes a carrier detection sensor configured to detect the carrier. The electric equipment further includes: a radio circuit; a channel switcher configured to switch a channel of radio communication by the radio circuit to a first channel or a second channel in response to the input switching command on condition that the normal operation mode is not in the locked state; and first and second carrier detection sensors as the carrier detection sensor. The switching command is determined as the second switching command or the third switching command depending on one of a difference in a detection length that is a time during which the carrier detection sensor continuously detects the carrier, and a difference as to which of the first and second carrier detection sensors detects the carrier, and a command as to whether the first channel or the second channel is to be used is determined by another difference.

MODE FOR CARRYING OUT THE INVENTION

Figure 1:
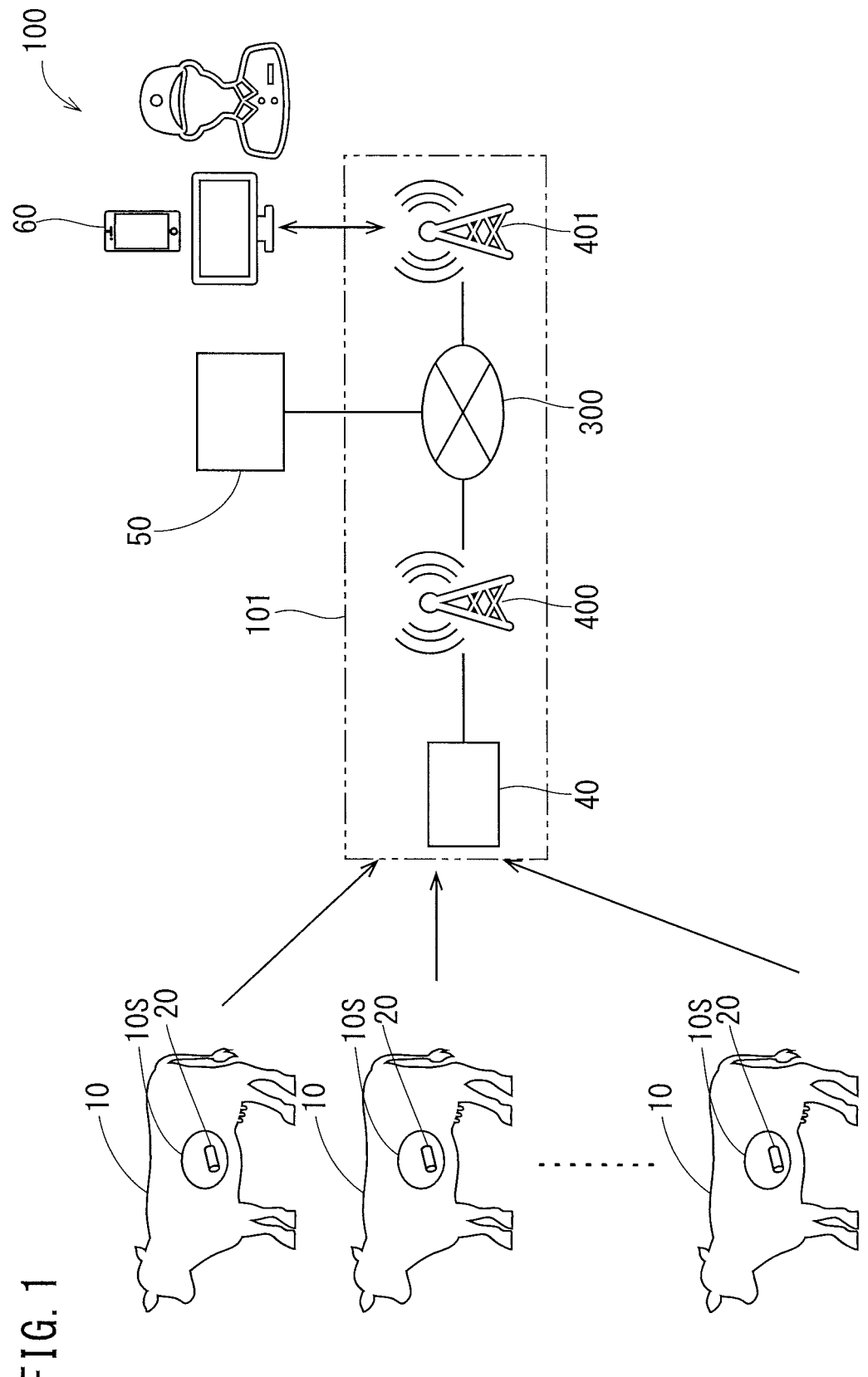
FIG. 1 is a schematic diagram illustrating an overall configuration of a monitoring system according to an embodiment of the present disclosure.

An embodiment of a monitoring system 100 of the present disclosure will be described with reference to FIGS. 1 to 6. The monitoring system 100 of the present embodiment illustrated in FIG. 1 includes a plurality of slave terminals 20 that are placed in stomachs 10S (specifically, first stomachs or second stomachs) of a plurality of cows 10 as monitoring targets, a master terminal 40, and a monitoring terminal 50. These terminals are connected together via a communication network 101 including radio base stations 400 and 401. The plurality of slave terminals 20 acquire and wirelessly transmit data related to states in the stomachs 10S of the cows 10, and those data are received by the master terminal 40 and collected in the monitoring terminal 50. Note that the slave terminal 20 corresponds to "electric equipment" in the claims.

Figure 2:
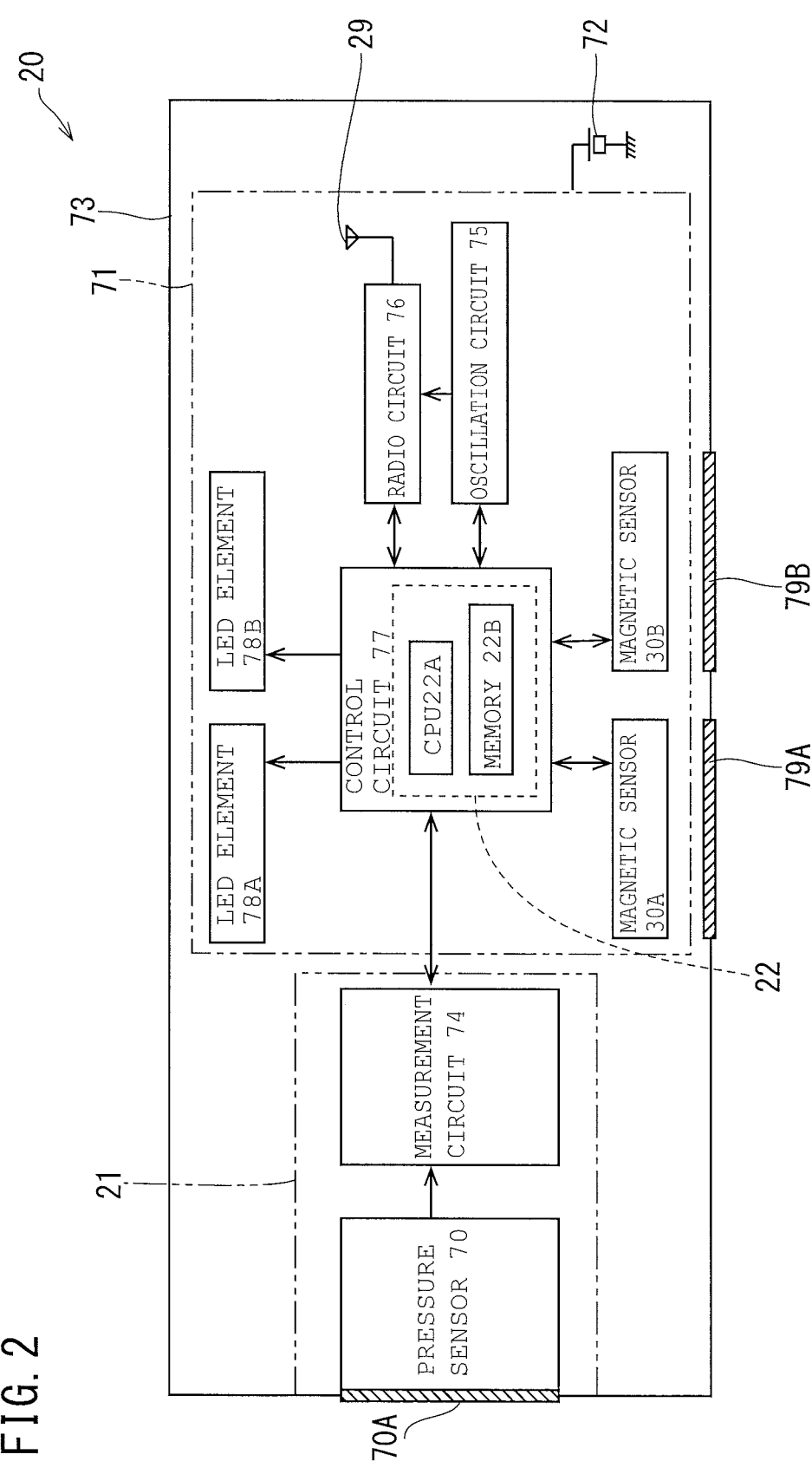
FIG. 2 is a block diagram illustrating an electrical configuration of a slave terminal.

As illustrated in FIG. 2, the slave terminal 20 includes a pressure sensor 70, a circuit board 71, a battery 72, and the like, which are hermetically accommodated in a housing 73 in a waterproof state so as to be protected from gastric acid or the like in the stomach 10S.

Figure 3A:
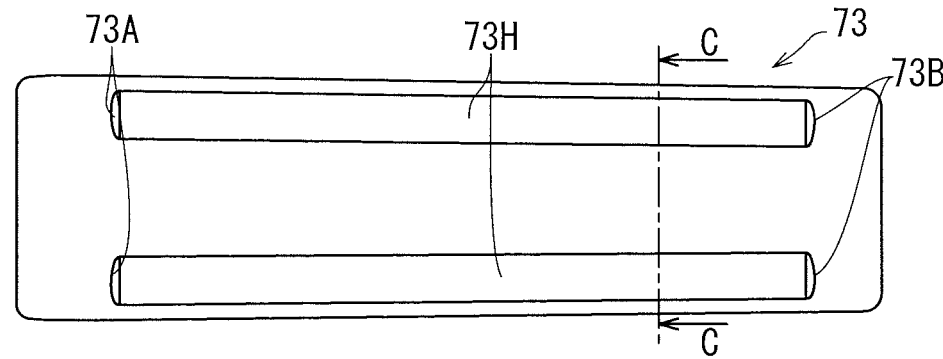
FIG. 3(A) is a front view of the slave terminal.
Figure 3B:
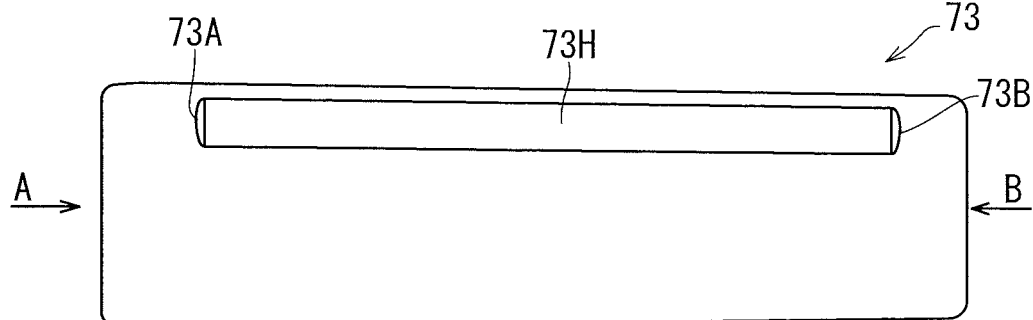
FIG. 3(B) is a side view of the slave terminal.
Figure 3C:
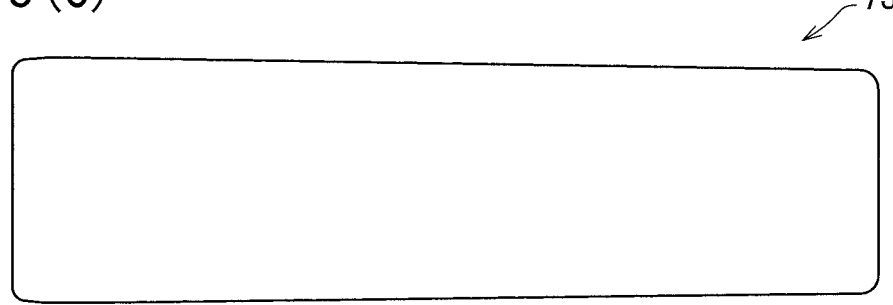
FIG. 3(C) is a rear view of the slave terminal.
Figure 4:
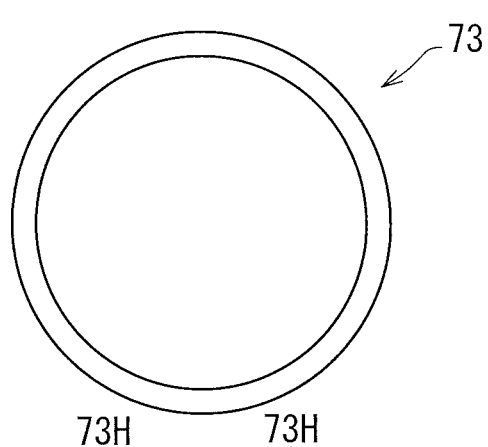
FIG. 4(A) is a drawing of the slave terminal in FIG. 3(B) as viewed from a direction A.
FIG. 4(B) is a drawing of the slave terminal in FIG. 3(B) as viewed from a direction B.
FIG. 4(C) is a cross-sectional view taken along C-C in FIG. 3(A)
FIG. 4(D) is a cross-sectional view taken along D-D in FIG. 4(C).
Figure 4:
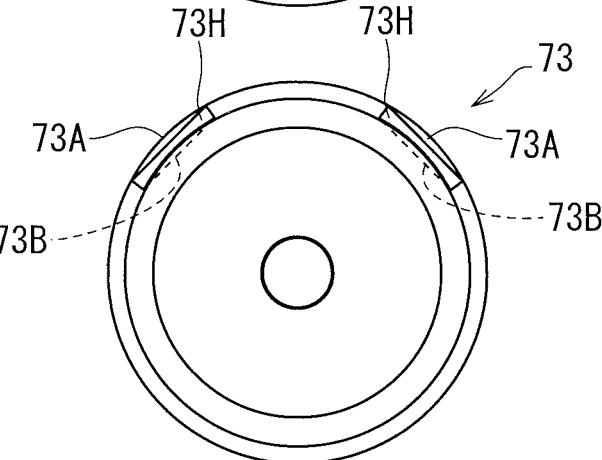
Figure 4:
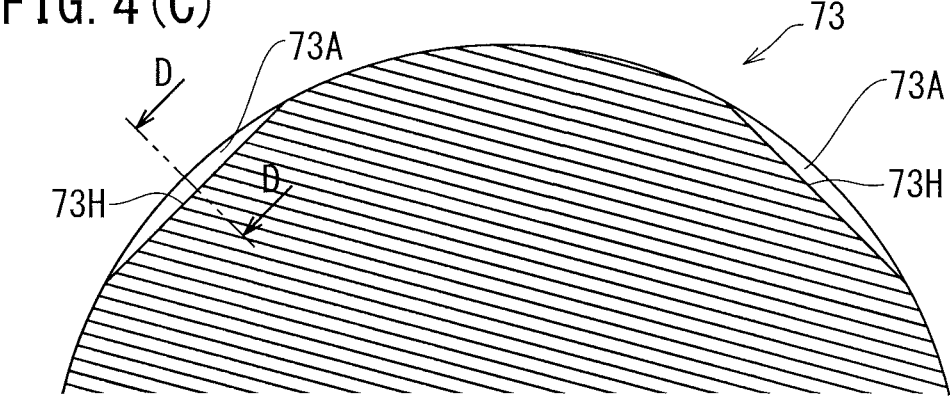
Figure 4:
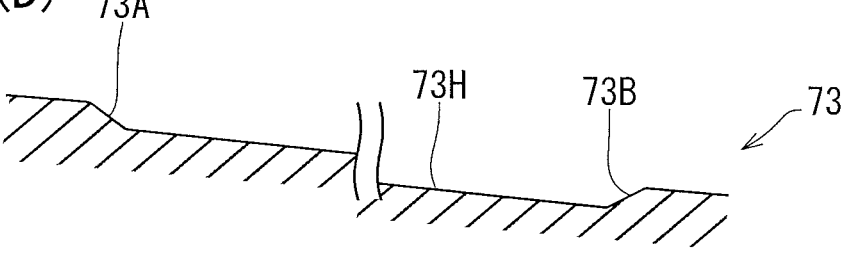

The housing 73 is, for example, a resin molded article. As illustrated in FIGS. 3 and 4, the housing 73 has a cylindrical shape with both ends closed, the cylindrical shape being gradually reduced in diameter from one end toward the other end (the left side in FIG. 3 is the one end), and has a plane symmetry along the axis. In addition, as illustrated in FIGS. 3(A) and 3(B), a pair of belt-shaped flat surfaces 73H that is cut flat in the axial direction is formed on an outer peripheral surface of the housing 73. Although not illustrated, a first sensing area 79A and a second sensing area 79B to be described later are provided on the pair of flat surfaces 73H, respectively. Note that stepped portions 73A and 73B between the outer peripheral surface of the housing 73 and the flat surfaces 73H are inclined surfaces (see FIGS. 4(B) and 4(C)).

As illustrated in FIG. 2, a pressure receiving surface 70A of the pressure sensor 70 is exposed to the outside of the housing 73, and a measurement unit 21 including the pressure sensor 70 and a measurement circuit 74 measures a pressure in the stomach 10S, which is one of the states of the cow 10. The pressure sensor 70 corresponds to a "monitoring sensor" in the claims.

An oscillation circuit 75, a radio circuit 76, a control circuit 77, and the like are mounted on the circuit board 71. The oscillation circuit 75 includes an oscillator as a main part, and gives a periodic signal that serves as a base of measurement of a radio carrier and time to the radio circuit 76 and the control circuit 77. The radio circuit 76 transmits and receives a radio signal, and includes an antenna 29 that is a coil antenna printed on the circuit board 71, for example. In the present embodiment, a plurality of channels that can be used for communication by the radio circuit 76 are prepared, and one of the channels is selected and used according to a surrounding situation of channel use. In the present embodiment, one channel is selected and used from channels CH1 and CH2.

Magnetic sensors 30A and 30B are also mounted on the circuit board 71. The magnetic sensors 30A and 30B are constituted by a Hall element such as a Hall IC, for example. In the present embodiment, a bipolar detection Hall element that detects both of an S-pole and an N-pole is used. The magnetic sensors 30A and 30B are respectively disposed at positions close to the first sensing area 79A and the second sensing area 79B described above, and detect magnetism when, for example, a magnet or the like is brought close to the first detection area 79A and the second detection area 79B, respectively. The magnetic sensors 30A and 30B output the detected magnetism to the control circuit 77 as a magnetism detection signal. As the magnetic sensors 30A and 30B, for example, a reed switch, a coil, a magnetoresistive element, a superconducting quantum interference device, or the like may be used instead of the Hall element.

The magnetic sensors 30A and 30B correspond to a "command input unit" and a "carrier detection sensor" in the claims.

LED elements 78A and 78B are also mounted on the circuit board 71. The LED elements 78A and 78B, which will be described later, indicate switching of an operation state of the slave terminal 20 to be described later to the outside by their lighting or blinking patterns. In the present embodiment, the LED elements 78A and 78B emit red and blue visible light, respectively. Here, at least a part of the housing 73 has translucency to allow light emitted from the LED elements 78A and 78B to pass therethrough. Note that an organic EL element may be mounted instead of the LED elements 78A and 78B. The LED elements 78A and 78B correspond to a "lighting indicator" in the claims.

As illustrated in FIG. 2, the control circuit 77 includes a microcomputer 22 including a CPU 22A and a memory 22B as a main part. The CPU 22A is connected to the measurement circuit 74, the oscillation circuit 75, the radio circuit 76, the LED elements 78A and 78B, and the like, and executes a predetermined transmission processing program or the like by controlling them. In addition, the magnetic sensors 30A and 30B are connected to an interrupt terminal of the CPU 22A. When the magnetic sensors 30A and 30B detect magnetism, the detected magnetism becomes an interrupt signal, and the CPU 22A executes a mode control program PG1 to be described later by interrupt processing. The memory 22B stores an identification number set for each slave terminal 20, the transmission processing program, the mode control program PG1, and the like.

The control circuit 77 operates by receiving power from the battery 72, and its operation state is switched between a normal operation mode and a sleep mode with reduced power consumption when the CPU 22A executes the mode control program PG1 by interrupt processing. When the control circuit 77 is switched to the sleep mode, power supply to components other than the CPU 22A, the magnetic sensors 30A and 30B, and the LED elements 78A and 78B is stopped. When the control circuit 77 is switched to the normal operation mode, power supply to the measurement circuit 74, the oscillation circuit 75, the radio circuit 76, and the like is started, and the CPU 22A repeatedly executes the transmission processing program at a predetermined cycle. The control circuit 77 corresponds to an "electric circuit" in the claims.

Figure 5:
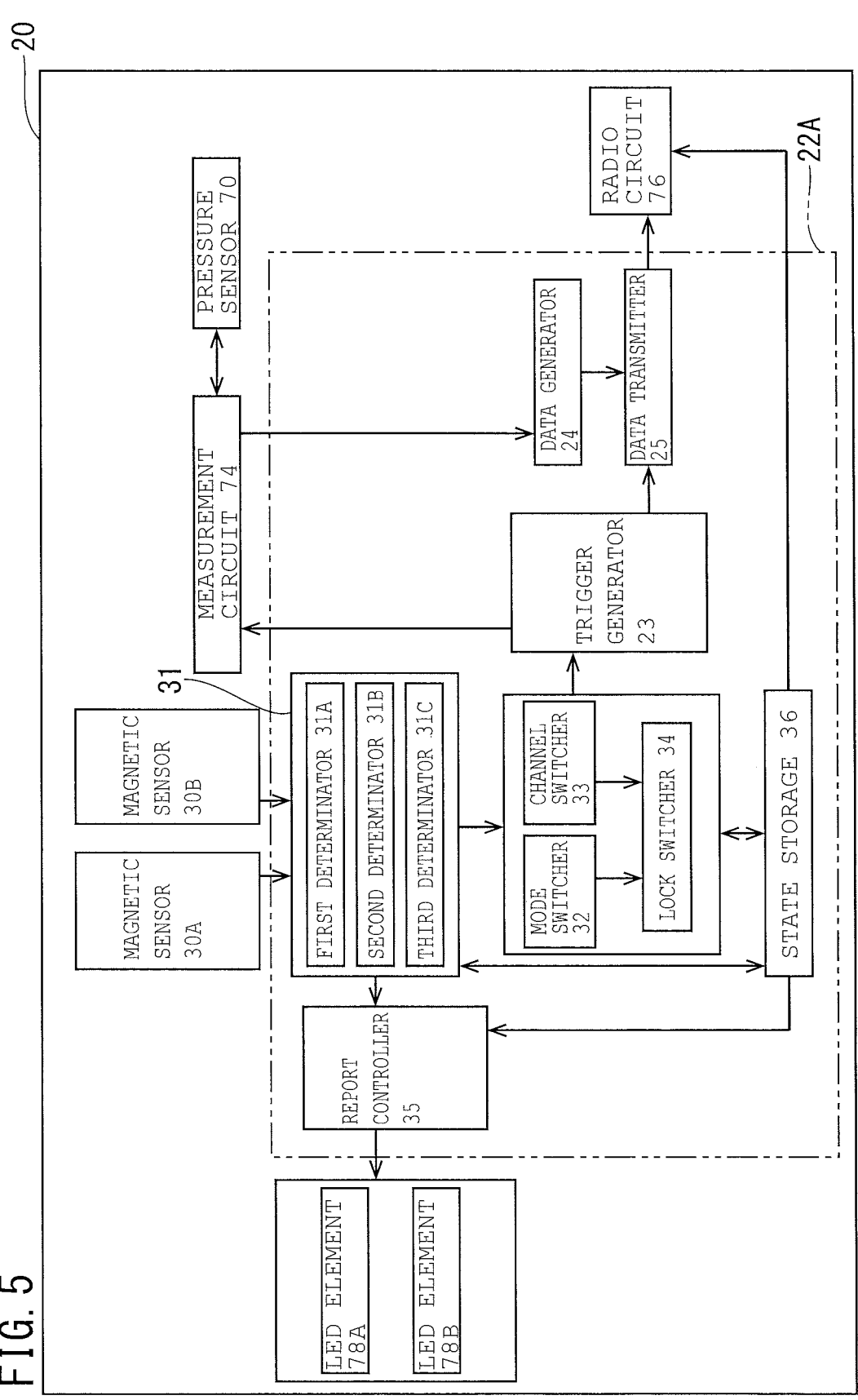
FIG. 5 is a block diagram illustrating a control configuration of the slave terminal.

FIG. 5 is a block diagram illustrating a control configuration of the slave terminal 20. A trigger generator 23, a data generator 24, a data transmitter 25, and the like, which have not been mentioned in the description of the structure of the slave terminal 20 described above, are configured by the CPU 22A executing the transmission processing program. In addition, a mode switcher 32, a channel switcher 33, a lock switcher 34, an indication controller 35, and the like are configured by the CPU 22A executing the mode control program PG1.

Specifically, when the CPU 22A executes the transmission processing program, the slave terminal 20 operates as follows. First, the trigger generator 23 generates a measurement trigger every certain period (for example, 1 [min]), and the pressure sensor 70 measures the pressure every time the measurement trigger is generated. The data generator 24 receives a measurement result of the pressure sensor 70 from the measurement circuit 74, converts the measurement result into a digital signal to generate pressure data D1, and gives the pressure data D1 to the data transmitter 25.

The data transmitter 25 stores the identification number of the slave terminal 20 and the pressure data D1 in a data frame having a predetermined data length, and generates transmission data D2. Here, the memory 22B temporarily accumulates the pressure data D1 generated by the data generator 24 in the memory 22B, and the data transmitter 25 stores, in the transmission data D2, the plurality of pieces of pressure data D1 read from the memory 22B (in the present embodiment, stores, for example, 10 pieces of pressure data D1). The trigger generator 23 generates a transmission trigger every predetermined period (for example, 10 [min]), and the data transmitter 25 wirelessly transmits the generated transmission data D2 using the radio circuit 76 every time the transmission trigger is generated. The transmission data D2 wirelessly transmitted by the plurality of slave terminals 20 are received by one master terminal 40. Here, the data transmitter 25 transmits the same transmission data D2 a plurality of times every time the transmission trigger is generated. This avoids a situation in which a transmission timing of the transmission data D2 of one slave terminal 20 and a transmission timing of another slave terminal 20 overlap with each other and the transmission data D2 are not received by the master terminal 40. In the present embodiment, for example, transmission is performed five times at intervals of 0.6 [sec]. Note that the slave terminal 20 may be provided with a temperature sensor or an acceleration sensor in addition to the pressure sensor 70, and may be configured to wirelessly transmit information other than the pressure in the stomach 10S as the state of the cow 10. Note that the data transmitter 25 corresponds to a "radio controller" in the claims.

The master terminal 40 has a function as a relay base station and a function of protocol conversion, and is installed, for example, in a cattle barn or a farm where the plurality of cows 10 are raised. The master terminal 40 transmits the transmission data D2 received from the slave terminals 20 to the monitoring terminal 50 via a general-purpose communication line 300. In the present embodiment, one master terminal 40 is connected to one monitoring terminal 50. However, for example, the master terminal 40 may be installed in each cattle barn or each farm, and a plurality of the master terminals 40 may be connected to one monitoring terminal 50.

The monitoring terminal 50 is constituted by a computer such as a server computer or a personal computer, and for example, identifies the slave terminal 20 of the cow 10 having an abnormality on the basis of the pressure data D1 included in the transmission data D2 from the slave terminals 20, and notifies a user terminal 60 of the abnormality (see FIG. 1). Note that the monitoring terminal 50 may be a cloud server including a plurality of servers.

As described above, the mode control program PG1 switches the operation state of the control circuit 77 between the normal operation mode in which power is supplied to the measurement circuit 74, the oscillation circuit 75, the radio circuit 76, and the like to execute the transmission processing program, and the sleep mode in which the power supply to these circuits is stopped. Here, the housing 73 of the slave terminal 20 has a sealed structure as described above. Since the mode control program PG1 is executed when the magnetic sensors 30A and 30B included in the slave terminal 20 detect magnetism, the operation state of the control circuit 77 can be switched contactlessly only by bringing a magnet or the like close thereto from the outside. Therefore, for example, when it is not necessary to acquire and wirelessly transmit data related to the state of the cow 10 such as at the time of shipment of the slave terminal 20 after manufacturing of the slave terminal 20, the operation state of the control circuit 77 is set to the sleep mode. When the slave terminal 20 is put into the stomach 10S of the cow 10, the operation state can be switched to the normal operation mode.

Specifically, the magnetism of the magnet is input as a switching command to the magnetic sensors 30A and 30B, the detected magnetism becomes an interrupt signal, and the CPU 22A executes the mode control program PG1 by interrupt processing. In addition, in the present embodiment, the interrupt signal from the magnetic sensor 30A also serves as a signal for setting the channel to be used for communication by the radio circuit 76 to the channel CH1, and the interrupt signal from the magnetic sensor 30B also serves as a signal for setting the channel to the channel CH2.

Furthermore, in the present embodiment, the operation state can be switched to the normal operation mode in which the operation state is thereafter prohibited from being switched to the sleep mode even when the magnetic sensors 30A and 30B detect magnetism. Hereinafter, the normal operation mode prohibited from being returned to the sleep mode is referred to as "normal operation mode in a locked state", and the normal operation mode allowed to be returned to the sleep mode is referred to as "normal operation mode in an unlocked state". When the operation state is switched to the normal operation mode in the locked state, the channel set at this time is also kept in a locked state in which the channel is thereafter prohibited from being switched. When the control circuit 77 is switched to the sleep mode, the power supply to the magnetic sensors 30A and 30B is not stopped, but when the control circuit 77 is switched to the normal operation mode in the locked state, the power supply to the magnetic sensors 30A and 30B is stopped.

When the mode control program PG1 is executed, the CPU 22A functions as a switching determinator 31, the mode switcher 32, the channel switcher 33, the lock switcher 34, the indication controller 35, a state storage 36, and the like as illustrated in FIG. 5. The state storage 36 stores the operation state of the control circuit 77 and the set channel. Specifically, the operation state of the control circuit 77 and the channel are set by the switching determinator 31, the mode switcher 32, the channel switcher 33, and the lock switcher 34 described below executing processing, and are updated and stored every time the operation state and the channel are set.

The switching determinator 31 is executed when magnetism is input to the magnetic sensors 30A and 30B. The switching determinator 31 includes a first determinator 31A, a second determinator 31B, and a third determinator 31C, and all determination results are stored in the state storage 36.

The first determinator 31A determines the current operation state of the control circuit 77 and the set channel according to the state storage 36.

The second determinator 31B determines which one of the magnetic sensors 30A and 30B has detected magnetism, and determines whether the content of the switching command indicated by the detected magnetism is a mode switching command to switch the mode or a channel switching command to switch the channel. Specifically, in a case where the magnetic sensor 30A or 30B that has detected magnetism this time is the same as the magnetic sensor 30A or 30B that detected magnetism last time by comparison with the previous determination result of the second determinator 31B stored in the state storage 36, the switching command is determined as the mode switching command. In a case where the magnetic sensor 30A or 30B is different from the magnetic sensor 30A or 30B that detected magnetism last time, the switching command is determined as the channel switching command. Note that the mode switching command corresponds to a "first switching command" or a "second switching command" in the claims.

The third determinator 31C determines whether or not the content of the switching command indicated by the detected magnetism is a lock switching command to switch to the normal operation mode in the locked state. Specifically, in a case where a magnetism detection time during which the magnetic sensor 30A or 30B continuously detects magnetism is equal to or longer than a first reference time T1 (for example, 5 [sec]), the switching command is determined as the lock switching command. In a case where the magnetism detection time is shorter than the first reference time T1, the switching command is determined, not as the lock switching command, but as an unlocking command for keeping the operation state of the control circuit 77 in the unlocked state in which the operation state is thereafter allowed to be switched. Note that the magnetism detection time corresponds to a "detection length" in the claims, the first reference time T1 corresponds to a "reference length" in the claims, and the lock switching command corresponds to a "third switching command" in the claims.

The mode switcher 32 switches the operation state of the control circuit 77 on the basis of the determination results of the first determinator 31A and the second determinator 31B. Specifically, when any one of the magnetic sensors 30A and 30B consecutively detects magnetism (mode switching command), the operation state is switched between the normal operation mode and the sleep mode. That is, for example, suppose that the current operation state of the control circuit 77 is the normal operation mode. In this case, when the magnetic sensor 30A detected magnetism last time and the magnetic sensor 30A detects magnetism also this time, the operation state is switched to the sleep mode. At this time, when the magnetic sensor 30B detects magnetism this time, the switching command is the channel switching command. Thus, the normal operation mode is kept without switching the modes, and the channel is switched by the channel switcher 33 to be described later.

However, in the present embodiment, in a case where the current operation state of the control circuit 77 is the sleep mode, the operation state is switched to the normal operation mode no matter whether the switching command is the mode switching command or the channel switching command.

In addition, in a case where the current operation state of the control circuit 77 is the normal operation mode in the locked state, switching to the sleep mode is prohibited. Thus, the normal operation mode in the locked state is kept without switching the operation state.

The channel switcher 33 sets the channel to be used for communication by the radio circuit 76 on the basis of the determination results of the first determinator 31A and the second determinator 31B. As described above, the channel to be used can be set to any of the radio channels CH1 and CH2 depending on which of the magnetic sensors 30A and 30B detects magnetism. In the present embodiment, the channel CH1 is set when the magnetic sensor 30A detects magnetism, and the channel CH2 is set when the magnetic sensor 30B detects magnetism. Therefore, when the magnetic sensor 30A or 30B detecting magnetism last time is different from the magnetic sensor 30A or 30B detecting magnetism this time (channel switching command), the channel is switched. When any one of the magnetic sensors 30A and 30B consecutively detects magnetism (mode switching command), the previously set channel is kept.

After the mode switcher 32 and the channel switcher 33 are executed, the lock switcher 34 determines whether to switch the operation state to the normal operation mode in the locked state on the basis of the determination result of the third determinator 31C. Specifically, when the magnetism detection time is equal to or longer than the first reference time T1 (lock switching command), the operation state is switched to the normal operation mode in the locked state in which the operation state cannot be switched to the sleep mode thereafter. At this time, even in a case where the operation state has been switched to the sleep mode by the mode switcher 32, the operation state is switched to the normal operation mode in the locked state. On the other hand, when the magnetism detection time is shorter than the first reference time T1 (unlocking command), the operation state switched by the mode switcher 32 is kept.

In addition, in a case where the switching command is the lock switching command on the basis of the determination result of the third determinator 31C, the channel set by the channel switcher 33 is also kept in the locked state in which the channel cannot be changed thereafter. In a case where the switching command is the unlocking command, the set channel is kept in a state in which the channel can be switched by subsequent magnetism detection by the magnetic sensor 30A or 30B.

The operation state of the control circuit 77 and the channel set in this way are stored in the state storage 36. When the operation state of the control circuit 77 is switched to the normal operation mode, the power supply to the measurement circuit 74, the oscillation circuit 75, the radio circuit 76, and the like is started, and the CPU 22A repeatedly executes the transmission processing program at a predetermined cycle.

The indication controller 35 controls the LED elements 78A and 78B to turn on the LED elements 78A and 78B or change the blinking patterns thereof on the basis of the determination result of the switching determinator 31, and indicate the switching of the operation state of the control circuit 77 and the channel setting to the outside.

Specifically, first, on the basis of the determination by the second determinator 31B, the indication controller 35 blinks the LED element 78A at high speed at a first interval (for example, an interval of 0.5 [sec]) when the magnetic sensor 30A detects magnetism, and blinks the LED element 78B at high speed at the first interval when the magnetic sensor 30B detects magnetism. By this configuration, an operator is notified that the operation state of the control circuit 77 and/or the channel are/is switched due to the magnetism detection by the magnetic sensor 30A or 30B.

Next, on the basis of the determination by the third determinator 31C, the indication controller 35 changes a blinking state according to the magnetism detection time of the magnetic sensor 30A or 30B. Specifically, suppose that the detection of magnetism ends within shorter than the first reference time T1. In this case, when the current operation state of the control circuit 77 is the sleep mode according to the first determinator 31A, the LED element 78A or 78B is blinked at low speed at a second interval (for example, an interval of 1.0 [sec]) three times after the high-speed blinking at the first interval, and is then turned off. On the other hand, when the current operation state of the control circuit 77 is the normal operation mode, both the LED elements 78A and 78B are momentarily turned on after the high-speed blinking at the first interval, and are then turned off. By this configuration, the operator is notified whether the operation state of the control circuit 77 is switched from the sleep mode to the normal operation mode or from the normal operation mode to the sleep mode.

In addition, in a case where the detection of magnetism continues for the period of the first reference time T1 or longer, the indication controller 35 switches the LED element 78A or 78B from the high-speed blinking state at the first interval to a lighting state. Furthermore, when the detection of magnetism ends, the LED element 78A or 78B is blinked at low speed three times, and then turned off. By this configuration, the operator is notified that the operation state of the control circuit 77 has shifted to the normal operation mode in the locked state. In a case where the current operation state of the control circuit 77 is the normal operation mode in the locked state, the indication controller 35 keeps the LED elements 78A and 78B in the tuned off state. By this configuration, the operator is notified that the operation state is the normal operation mode in the locked state.

Figure 6:
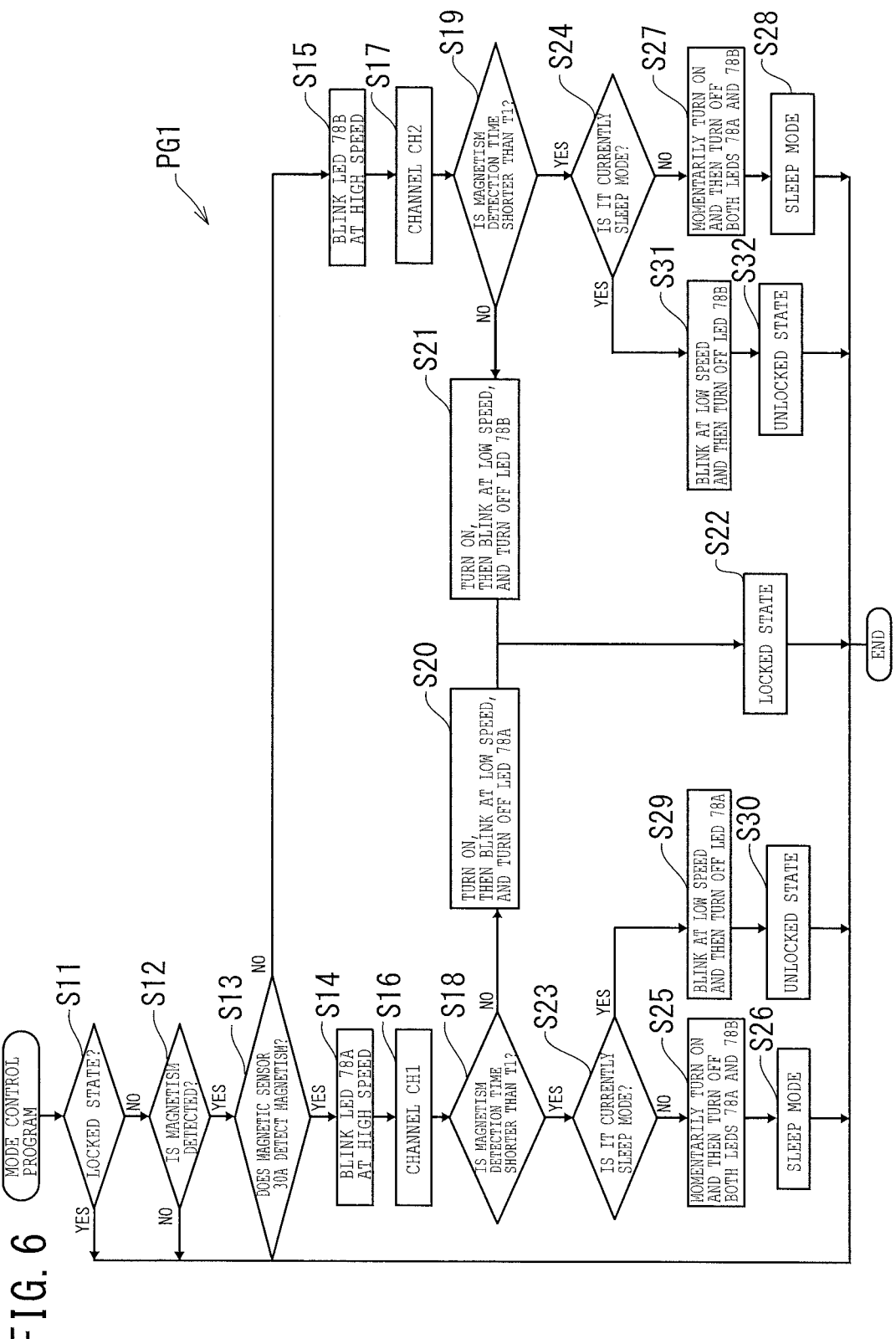
FIG. 6 is a flowchart of a mode control program.

Hereinafter, an example of the mode control program PG1 executed by the CPU 22A of the slave terminal 20 is illustrated in FIG. 6. As described above, the mode control program PG1 is executed when the magnetic sensor 30A or 30B detects magnetism and the detected magnetism is input to the CPU 22A as an interrupt signal (YES in S12). In the first place, in a case where the operation state of the control circuit 77 is set to the normal operation mode in the locked state, the power supply to the magnetic sensors 30A and 30B is stopped and no magnetism is detected. Thus, the mode control program PG1 is not executed (YES in S11). In step S13, it is determined which of the magnetic sensors 30A and 30B has detected magnetism (S13). The LED element 78A is blinked at high speed (S14) when the magnetic sensor 30A detects magnetism (YES in S13). The LED element 78B is blinked at high speed (S15) when the magnetic sensor 30B detects magnetism (NO in S13). An operator is thus notified that the operation state of the control circuit 77 and/or the channel are/is switched.

Next, when the magnetic sensor 30A detects magnetism (YES in S13), the channel to be used by the radio circuit 76 is set to the channel CH1 (S16). When the magnetic sensor 30B detects magnetism (NO in S13), the channel is set to the channel CH2 (S17).

Then, it is determined whether the detection of magnetism is equal to or longer than the first reference time T1, or shorter than the first reference time T1 (S18, S19). In a case where the detection of magnetism is equal to or longer than the first reference time T1 (NO in S18, NO in S19), the LED element 78A is shifted to the lighting state, further blinked at low speed three times, and then turned off for the magnetism detection by the magnetic sensor 30A (NO in S18), and the LED element 78B is shifted to the lighting state, further blinked at low speed three times, and then turned off for the magnetism detection by the magnetic sensor 30B (NO in S19) (S20, S21). Subsequently, the operation state of the control circuit 77 is switched to the normal operation mode in the locked state (S22), and the mode control program PG1 is terminated.

On the other hand, in a case where the detection of magnetism is shorter than the first reference time T1 (YES in S18, YES in S19), the current operation state of the control circuit 77 is determined (S23, S24). In a case where the current operation state of the control circuit 77 is the normal operation mode in the unlocked state (NO in S23, NO in S24), both the LED elements 78A and 78B are momentarily turned on and then turned off (S25, S27), the operation state of the control circuit 77 is switched to the sleep mode (S26, S28), and the mode control program PG1 is terminated.

In a case where the current operation state of the control circuit 77 is the sleep mode (YES in S23, YES in S24), the LED element 78A is blinked at low speed three times and then turned off for the magnetism detection by the magnetic sensor 30A (YES in S23), and the LED element 78B is blinked at low speed three times and then turned off for the magnetism detection by the magnetic sensor 30B (YES in S24) (S29, S31). Subsequently, the operation state of the control circuit 77 is switched to the normal operation mode in the unlocked state (S30, S32), and the mode control program PG1 is terminated.

Here, steps S11, S23, and S24 correspond to the "first determinator 31A" of the CPU 22A, step S13 corresponds to the "second determinator 31B" of the CPU 22A, steps S18 and S19 correspond to the "third determinator 31C" of the CPU 22A, steps S26, S28, and S32 correspond to the "mode switcher 32" of the CPU 22A, steps S16 and S17 correspond to the "channel switcher 33" of the CPU 22A, step S22 corresponds to the "lock switcher 34" of the CPU 22A, and steps S14, S15, S20, S21, S25, S27, S29, S30, and S31 correspond to the "indication controller 35" of the CPU 22A.

The configuration of the monitoring system 100 of the present embodiment has been described above. According to the monitoring system 100 using the plurality of slave terminals 20 of the present embodiment, the slave terminals 20 acquire data related to the states in the stomachs 10S of the cows 10 as the monitoring targets, and wirelessly transmit the data to the master terminal 40, and the data are collected in the monitoring terminal 50 from the master terminal 40. Therefore, the monitoring terminal 50 can collectively monitor changes in the states of the plurality of cows 10.

The slave terminal 20 of the present embodiment includes the magnetic sensors 30A and 30B. When a magnet is brought close to the first sensing area 79A and the second sensing area 79B provided on the outer peripheral surface of the housing 73, the slave terminal 20 detects the magnetism of the magnet, and switches the operation state of the control circuit 77 between the normal operation mode in which power is supplied to those parts that acquire and wirelessly transmit the data related to the state in the stomach 10S, and the sleep mode in which the power supply to the parts is stopped. As a result, the operation state can be switched contactlessly from the outside after manufacturing of the slave terminal 20. Thus, for example, the operation state of the control circuit 77 can be switched to the sleep mode when it is not necessary to acquire and wirelessly transmit the data related to the state of the cow 10 such as at the time of shipment of the slave terminal 20, and the operation state can be switched to the normal operation mode when the slave terminal 20 is put into the stomach 10S of the cow 10.

Here, the cow 10, which is a ruminant animal, may ingest a metal foreign substance (nail, wire, or the like) mixed in feed into the stomach 10S together with the feed, and may thereby have a wound disease. In order to prevent such a disease, a magnet for removing metal foreign substances may be put into the stomach 10S of the cow 10 in advance to attract the ingested metal foreign substance to the magnet. When the slave terminal 20 is put into the stomach 10S of the cow 10 having such a magnet for removing metal foreign substances therein, there is a problem that the magnetic sensors 30A and 30B of the slave terminal 20 detect the magnetism of the magnet for removing metal foreign substances in the stomach 10S, and the operation state of the control circuit 77 is unintentionally switched from the normal operation mode to the sleep mode, which makes it impossible to acquire and wirelessly transmit the data related to the state in the stomach 10S. To cope with this, the slave terminal 20 of the present embodiment can switch the operation state to the normal operation mode in the locked state in which the operation state is prohibited from being switched to the sleep mode even when the magnetic sensors 30A and 30B detect magnetism. As a result, even for the cow 10 having swallowed the magnet for removing metal foreign substances, it is possible to prevent the switching to the sleep mode even when the magnetic sensors 30A and 30B detect the magnetism of the magnet for removing metal foreign substances in the stomach 10S by putting the slave terminal 20 into the stomach 10S after switching the operation state to the normal operation mode in the locked state. Accordingly, it becomes possible to stably acquire and wirelessly transmit the data related to the state in the stomach 10S.

In addition, in the present embodiment, it is also possible to switch the operation state to the normal operation mode in the unlocked state that is not kept in the locked state. Thus, for example, after the slave terminal 20 is manufactured and before the slave terminal 20 is put into the stomach 10S of the cow 10, it is possible to switch the operation state between the normal operation mode in the unlocked state and the sleep mode as necessary and to check the operation of wireless transmission, for example.

In addition, in the slave terminal 20 of the present embodiment, the operation state is switched to the normal operation mode in the locked state when the magnetic sensor 30A or 30B continuously detects magnetism for the period of the first reference time T1 or longer. The magnetism detection time is longer than that of when the operation state is switched to the normal operation mode in the unlocked state or the sleep mode. As described above, since the switching to the normal operation mode in the locked state is performed by a magnetism input mode that is less likely to occur than the switching to the normal operation mode in the unlocked state or the sleep mode, it is possible to prevent unintentional switching to the normal operation mode in the locked state under the influence of disturbance.

In addition, the slave terminal 20 of the present embodiment includes the two magnetic sensors 30A and 30B, and can switch the channels CH1 and CH2 of radio communication depending on which of the magnetic sensors 30A and 30B has detected magnetism. The operation state of the control circuit 77 can be switched between the sleep mode and the normal operation mode by one of the magnetic sensors 30A and 30B consecutively detecting magnetism. Furthermore, as described above, the operation state can be shifted to the normal operation mode in the locked state depending on the difference in the time during which magnetism is continuously detected. As described above, in the present embodiment, the plurality of magnetic sensors 30A and 30B are provided, and the combination of the magnetic sensors 30A and 30B for detecting magnetism and the time for continuously detecting magnetism are changed, so that not only the operation state of the control circuit 77 but also the channel can be switched at the same time.

In addition, in the slave terminal 20 of the present embodiment, the LED elements 78A and 78B indicate whether the operation state of the control circuit 77 has been switched to the sleep mode or the normal operation mode. Since the combination of the LED elements 78A and 78B and the lighting or lighting pattern of each of the LED elements 78A and 78B are changed at the time of switching, switching among the normal operation mode in the locked state, the normal operation mode in the unlocked state, and the sleep mode can be distinguished and notified to the outside.

OTHER EMBODIMENTS (1) In the slave terminal 20 of the above embodiment, the magnetism input time to the magnetic sensors 30A and 30B is shorter than the common first reference time T1 in both cases where the operation state of the control circuit 77 is switched from the normal operation mode in the unlocked state to the sleep mode and where the operation state is switched from the sleep mode to the normal operation mode in the unlocked state. However, the magnetism input reference time may be different.

(2) In the slave terminal 20 of the above embodiment, the magnetism input time to the magnetic sensors 30A and 30B is different between when the operation state is switched to the normal operation mode in the locked state and when the operation state is switched to the normal operation mode in the unlocked state. However, the magnetism input mode to the magnetic sensors 30A and 30B may be different other than the time. For example, magnetism may be consecutively brought close to the magnetic sensors 30A and 30B a plurality of times at different intervals. In this case, when the operation state is switched to the normal operation mode in the locked state, a complicated input mode that cannot normally occur is adopted. The operation state is thereby switched by the input mode that is less likely to occur than the switching to the normal operation mode in the unlocked state. Therefore, with this configuration, it is also possible to prevent unintentional switching to the normal operation mode in the locked state.

(3) The slave terminal 20 of the above embodiment has a configuration in which the operation state cannot be switched to the sleep mode once switched to the normal operation mode in the locked state. However, the operation state may be switched to the sleep mode in a case where the magnetism input time to the magnetic sensors 30A and 30B is equal to or longer than the first reference time T1, or by setting a second reference time longer than the first reference time T1, or a complicated magnetism input mode that cannot normally occur.

(4) In the slave terminal 20 of the above embodiment, the channel is switched depending on which of the magnetic sensors 30A and 30B has detected magnetism, and the operation state of the control circuit 77 is switched between the sleep mode and the normal operation mode by any one of the magnetic sensors 30A and 30B consecutively detecting magnetism. However, the operation state of the control circuit 77 may be switched depending on which of the magnetic sensors 30A and 30B has detected magnetism, and the channel may be switched by any one of the magnetic sensors 30A and 30B consecutively detecting magnetism.

In addition, the configuration in which a different combination of the magnetic sensors 30A and 30B for detecting magnetism and a different input mode of magnetism to the magnetic sensors 30A and 30B adopted for switching the operation state of the control circuit 77 and the channel are not limited to the above-described configuration. For example, when one of the magnetic sensors 30A and 30B detects magnetism, only the operation state of the control circuit 77 may be switched, and when the other of the magnetic sensors 30A and 30B detects magnetism, only the channel may be switched. In this case, the magnetism detection modes of the magnetic sensor 30A and the magnetic sensor 30B may be the same or different. In addition, when the operation state of the control circuit 77 is switched to the locked state, the channel may also be kept in the locked state, or the channel may be switched to the locked state separately from the switching of the operation state of the control circuit 77 to the locked state.

(5) The slave terminal 20 of the above embodiment is configured to switch the channel used for radio communication between the channels CH1 and CH2 by the magnetism detection by the magnetic sensors 30A and 30B. However, the channel may be switched among three or more channels.

(6) The slave terminal 20 of the above embodiment includes the channel switcher 33 and is configured to switch the channel used for radio communication by the magnetism detection by the magnetic sensors 30A and 30B. However, the slave terminal 20 may be configured to switch only the operation state of the control circuit 77 by the magnetism detection without including the channel switcher 33. In this case, the number of magnetic sensors 30A and 30B may be one.

(7) In the slave terminal 20 of the above embodiment, whether the operation state of the control circuit 77 has been switched to the sleep mode or the normal operation mode is indicated by turning on the LED elements 78A and 78B or changing the lighting patterns thereof. However, the present configuration is not limited thereto, and for example, sound may be used. Alternatively, only the operation state being set to the normal operation mode in the locked state may be indicated. In addition, the set channel may also be indicated.

(8) In the above embodiment, the slave terminal 20 is configured to switch the operation state of the control circuit 77 and the channel used for radio communication when detecting magnetism from the outside. However, instead of magnetism, the slave terminal 20 may be configured to switch the operation state of the control circuit 77 and the channel used for radio communication when detecting radio waves, light including visible rays and infrared rays, or sound waves having a special wavelength such as ultrasonic waves.

Although specific examples of the technology included in the claims are disclosed in the present specification and the drawings, the technology described in the claims is not limited to these specific examples, and includes those obtained by variously modifying and changing the specific examples, and also includes those obtained by singly extracting a part from the specific examples.

DESCRIPTION OF THE REFERENCE NUMERALS

10 Cow (animal)
10S Stomach
20 Slave terminal (electric equipment)
25 Data transmitter (radio controller)
30A, 30B Magnetic sensor (command input unit, carrier detection sensor)
32 Mode switcher
33 Channel switcher
70 Pressure sensor (monitoring sensor)
73 Housing
76 Radio circuit
77 Control circuit (electric circuit)
78A, 78B LED element (lighting indicator)
CH1, CH2 Channel
T1 First reference time (reference length)

The invention claimed is:

1. Electric equipment comprising:
a command input unit to which a switching command is input contactlessly from an outside; and a mode switcher configured to switch an electric circuit of the electric equipment between a normal operation mode and a sleep mode in response to the input switching command, wherein
the normal operation mode includes the normal operation mode in an unlocked state in which switching to the sleep mode is allowed, and the normal operation mode in a locked state in which switching to the sleep mode is prohibited, and
the switching command includes
a first switching operation for switching the normal operation mode to the sleep mode,
a second switching operation for switching the sleep mode to the normal operation mode and keeping the normal operation mode in the unlocked state, and
a third switching operation for switching the sleep mode to the normal operation mode and keeping the normal operation mode in the locked state, the third switching command having a longer input time or a more complicated input mode to the command input unit than an input time or an input mode of the second switching command,
the switching command uses any one of magnetism, light, or a sound wave as a carrier,
the command input unit includes a carrier detection sensor configured to detect the carrier,
the switching command has a different command content depending on a difference in a detection length that is a time during which the carrier detection sensor continuously detects the carrier, and
the switching command having the detection length shorter than a predetermined reference length is the second switching command, and the switching command having the detection length equal to or longer than the reference length is the third switching command.

2. The electric equipment according to claim 1, comprising a lighting indicator configured to indicate, with different lighting patterns, whether the electric circuit has been switched to the normal operation mode or the sleep mode.

3. The electric equipment according to claim 1, comprising a plurality of the carrier detection sensors, wherein
the switching command has a different command content depending on which of the carrier detection sensors detects the carrier.

4. The electric equipment according to claim 3, comprising:
a radio circuit; and
a channel switcher configured to switch a channel of radio communication by the radio circuit in response to the input switching command on condition that the normal operation mode is not in the locked state, wherein
a command as to which channel is to be used is determined depending on which of the carrier detection sensors detects the carrier.

5. Electric equipment comprising:
a command input unit to which a switching command is input contactlessly from an outside; and a mode switcher configured to switch an electric circuit of the electric equipment between a normal operation mode and a sleep mode in response to the input switching command, wherein

15 the normal operation mode includes the normal operation mode in an unlocked state in which switching to the sleep mode is allowed, and the normal operation mode in a locked state in which switching to the sleep mode is prohibited, and the switching command includes
  a first switching operation for switching the normal operation mode to the sleep mode,
  a second switching operation for switching the sleep mode to the normal operation mode and keeping the normal operation mode in the unlocked state, and
  a third switching operation for switching the sleep mode to the normal operation mode and keeping the normal operation mode in the locked state, the third switching operation having a longer input time or a more complicated input mode to the command input unit than an input time or an input mode of the second switching operation, the switching command uses any one of magnetism, light, or a sound wave as a carrier, the command input unit includes a carrier detection sensor configured to detect the carrier, and the electric equipment further comprising:
  a radio circuit;
  a channel switcher configured to switch a channel of radio communication by the radio circuit to a first channel or a second channel in response to the input switching command on condition that the normal operation mode is not in the locked state; and
  first and second carrier detection sensors as the carrier detection sensor, wherein the switching command is determined as the second switching operation or the third switching operation depending on one of a difference in a detection length that is a time during which the carrier detection sensor continuously detects the carrier, and a difference as to which of the first and second carrier detection sensors detects the carrier, and a command as to whether the first channel or the second channel is to be used is determined by another difference.

6. The electric equipment according to claim 5, wherein the switching command has a different command content depending on a difference in a detection length that is a time during which the carrier detection sensor continuously detects the carrier.

7. The electric equipment according to claim 5, comprising a lighting indicator configured to indicate, with different lighting patterns, whether the electric circuit has been switched to the normal operation mode or the sleep mode.

8. The electric equipment according to claim 5, comprising a plurality of the carrier detection sensors, wherein
  the switching command has a different command content depending on which of the carrier detection sensors detects the carrier.

9. The electric equipment according to claim 8, comprising:
  a radio circuit; and
  a channel switcher configured to switch a channel of radio communication by the radio circuit in response to the input switching command on condition that the normal operation mode is not in the locked state, wherein
  a command as to which channel is to be used is determined depending on which of the carrier detection sensors detects the carrier.

10. The electric equipment according to claim 5, comprising:
  a housing accommodating the electric circuit in a waterproof state;
  a monitoring sensor configured to measure a physical quantity related to an environment outside the housing; and
  a radio controller configured to cause the radio circuit to wirelessly transmit a measurement result of the monitoring sensor.

11. The electric equipment according to claim 10, wherein the switching command has a different command content depending on a difference in a detection length that is a time during which the carrier detection sensor continuously detects the carrier.

12. The electric equipment according to claim 10, comprising a lighting indicator configured to indicate, with different lighting patterns, whether the electric circuit has been switched to the normal operation mode or the sleep mode.

13. The electric equipment according to claim 10, comprising a plurality of the carrier detection sensors, wherein
  the switching command has a different command content depending on which of the carrier detection sensors detects the carrier.

14. The electric equipment according to claim 13, comprising:
  a radio circuit; and
  a channel switcher configured to switch a channel of radio communication by the radio circuit in response to the input switching command on condition that the normal operation mode is not in the locked state, wherein
  a command as to which channel is to be used is determined depending on which of the carrier detection sensors detects the carrier.

15. The electric equipment according to claim 10, wherein the electric equipment is put into a stomach of an animal, and the monitoring sensor measures a physical quantity related to an environment inside the stomach.

16. The electric equipment according to claim 15, wherein the switching command has a different command content depending on a difference in a detection length that is a time during which the carrier detection sensor continuously detects the carrier.

17. The electric equipment according to claim 15, comprising a lighting indicator configured to indicate, with different lighting patterns, whether the electric circuit has been switched to the normal operation mode or the sleep mode.

18. The electric equipment according to claim 6, comprising a plurality of the carrier detection sensors, wherein
  the switching command has a different command content depending on which of the carrier detection sensors detects the carrier.

19. The electric equipment according to claim 18, comprising:
  a radio circuit; and
  a channel switcher configured to switch a channel of radio communication by the radio circuit in response to the input switching command on condition that the normal operation mode is not in the locked state, wherein
  a command as to which channel is to be used is determined depending on which of the carrier detection sensors detects the carrier.

* * * * *